US012582983B2

(12) United States Patent
Pflimlin et al.

(10) Patent No.: US 12,582,983 B2
(45) Date of Patent: Mar. 24, 2026

(54) METHOD FOR MANUFACTURING A BIOLOGICAL ANALYSIS CHIP AND BIOLOGICAL ANALYSIS CHIP

(71) Applicant: PRECIPHOS, Strasbourg (FR)

(72) Inventors: Pascal Pflimlin, Baldersheim (FR); Bernard Ludwig, Plan-les-Ouates (CH)

(73) Assignee: PRECIPHOS, Strasbourg (FR)

( * ) Notice: Subject to any disclaimer, the term of this patent is extended or adjusted under 35 U.S.C. 154(b) by 490 days.

(21) Appl. No.: 18/252,023

(22) PCT Filed: Nov. 4, 2021

(86) PCT No.: PCT/EP2021/080625
§ 371 (c)(1),
(2) Date: May 5, 2023

(87) PCT Pub. No.: WO2022/096566
PCT Pub. Date: May 12, 2022

(65) Prior Publication Data
US 2023/0415149 A1 Dec. 28, 2023

(30) Foreign Application Priority Data
Nov. 6, 2020 (FR) ...................................... 2011447

(51) Int. Cl.
*B01L 3/00* (2006.01)
*B01L 9/00* (2006.01)
*G01N 33/543* (2006.01)

(52) U.S. Cl.
CPC ..... *B01L 3/50255* (2013.01); *B01L 3/502707* (2013.01); *B01L 3/502753* (2013.01);
(Continued)

(58) Field of Classification Search
CPC ................. G06F 12/0891; G06F 13/16; B01L 2300/0681; B01L 2300/0829;
(Continued)

(56) References Cited

U.S. PATENT DOCUMENTS 6,207,000 B1 3/2001 Schwobel et al.
2002/0094533 A1 7/2002 Hiess et al.
(Continued)

FOREIGN PATENT DOCUMENTS

CN 101759800 A 6/2010
CN 108037278 A 5/2018
(Continued)

OTHER PUBLICATIONS

International Search Report dated Feb. 1, 2022 for Application No. PCT/EP2021/080625.

*Primary Examiner* — Jennifer Wecker
*Assistant Examiner* — Jonathan Bortoli

(57) ABSTRACT

Disclosed is a method for manufacturing an analysis chip for analysing a biological sample (1), which method comprises providing two support matrices (10), in each of which at least one through hole has been formed (11); providing at least one sheet (13) of solid and porous analysis material; superposing, in the following order, a (lower) support matrix (10*a*), the sheet (6) of analysis material and an (upper) support matrix (10*b*); mechanically assembling the two support matrices (10) and the sheet (13) of analysis material, during which a pressing force is applied at right angles to the lower and upper surfaces of the support matrices (10) so as to bring the support matrices (10) closer to each other.

13 Claims, 5 Drawing Sheets

(52) U.S. Cl.
CPC .......... *B01L 9/52* (2013.01); *G01N 33/54366*
(2013.01); *B01L 2300/0681* (2013.01); *B01L*
*2300/0829* (2013.01); *B01L 2300/161*
(2013.01)

(58) Field of Classification Search
CPC .......... B01L 2300/161; B01L 3/50255; B01L
3/502707; B01L 3/502753; B01L 9/52;
G01N 33/54366
See application file for complete search history.

(56) References Cited

U.S. PATENT DOCUMENTS

| | | |
|---|---|---|
| 2003/0029787 A1 | 2/2003 | Liu et al. |
| 2004/0115707 A1 | 6/2004 | Amano |
| 2004/0171017 A1* | 9/2004 | Firrao .................. B01L 3/5085<br>436/518 |
| 2007/0184483 A1 | 8/2007 | Neriishi et al. |
| 2012/0329163 A1 | 12/2012 | Faber et al. |

FOREIGN PATENT DOCUMENTS

| | | |
|---|---|---|
| EP | 1332865 A1 | 8/2003 |
| EP | 1521084 A2 | 4/2005 |
| KR | 101355434 B1 | 1/2014 |
| WO | WO0119502 A2 | 3/2001 |
| WO | WO2004067176 A1 | 8/2004 |
| WO | WO2014053237 A1 | 4/2014 |
| WO | WO2020082029 A1 | 4/2020 |

* cited by examiner

METHOD FOR MANUFACTURING A BIOLOGICAL ANALYSIS CHIP AND BIOLOGICAL ANALYSIS CHIP

CROSS-REFERENCE TO RELATED APPLICATION

This application is a national stage application, filed under 35 U.S.C. § 371, of International Patent Application No. PCT/EP2021/080625, filed on Nov. 4, 2021, which claims the priority of French application No. FR2011447, the contents of which are incorporated by reference.

FIELD OF THE INVENTION

The present invention relates to the field of biological analyses, in particular biochemical analyses. More specifically, the invention relates to a process for manufacturing filtering chips, which can optionally be functionalized to carry out biological analyses.

TECHNOLOGICAL BACKGROUND

In the field of biological analyses, it is known to use protein chips ("protein microarrays") to study the biochemical activity of proteins. In such chips, a library of antibodies or protein fragments ("probes")— or even whole proteins— is placed on a matrix such as a glass slide. In this case, a single sample is tested on all the probes deposited on the matrix.

Biological analysis devices allowing the parallel analysis of several samples have also been developed. Document WO2014/053237 is an example in which a miniaturized device allows analysis of several biological samples simultaneously ("multiplex" analysis). Each sample can also be exposed to several different probes successively. In other words, the device allows an analysis of the "3D analysis" type. The device described by this document comprises a plurality of channels, into each of which a liquid phase sample can be injected independently of the other channels.

Each channel can be formed from several tubular portions. Between two successive portions an approximately cylindrical analysis zone formed in an appropriate matrix is inserted.

The analysis zones can in particular be formed in a flat nitrocellulose matrix, the entire surface of which, except for the analysis zones, is rendered hydrophobic by an impregnation of wax.

The analysis zones can simply consist of untreated nitrocellulose, so that they constitute filtration zones, or alternatively of nitrocellulose functionalized for example by means of a probe molecule.

The impregnation operation with wax makes it possible to delimit the analysis zones, but also to limit the lateral diffusion inside the matrix (that is to say outside a given analysis zone towards the other neighbouring analysis zones) of the molecules of interest (probe molecules or molecules of a sample). For this impregnation operation, a solid ink printing process is implemented, so as to deposit a layer of wax on the matrix in the areas that must be rendered hydrophobic. At the end of the printing, the matrix is heated to a temperature higher than the melting point of the used wax, then cooled, so that the wax diffuses laterally and in depth, in the thickness of the matrix, so as to limit its subsequent undesirable diffusion toward the analysis areas.

However, such a process does not make it possible to finely control the volume of a given analysis zone nor the shape of the surface which delimits this volume, as shown in the figures presented in that document. In particular, the circumference of the upper surface of a test site varies from site to site and is generally not circular so that, in the direction of flow, the section of the analysis area is not precisely the same as the interior section of the channel in which the analysis area is to be inserted.

Consequently, the precision of such a device is limited due to the manufacturing process used to form the analysis zones, and concomitantly, the limit of quantification remains too high for certain biological analyzes in which the concentrations involved (or their variations) are particularly low.

Document US2004/0115707 discloses a biochemical analysis unit comprising a base plate having a plurality of holes filled with a porous and adsorbent material so as to form a plurality of analysis zones. The filling of the holes can be obtained by laminating a sheet of adsorbent material on the previously drilled base plate.

During laminating, the sheet of analysis material is stressed anisotropically due to the tensile force exerted in the direction of lamination. The properties of the adsorbent material after insertion into the holes are therefore anisotropic. It is even possible that the thickness of the adsorbent material varies within the same hole.

Moreover, the lamination does not break the continuity of the sheet of adsorbent material. The adsorbent material therefore forms a continuous surface between two channels under or on the plate, as can be seen in FIG. 2b of document US2004/0115707. The molecules of interest (from the sample or probes) therefore risk diffusing from one channel 3 to another due to this continuity.

The precision and sensitivity of a quantitative analysis performed with such a plate are therefore limited. In another embodiment described by US2004/0115707, the adsorbent material can be dissolved in a solvent. The solution obtained is then injected into the holes and the solvent evaporated. This liquid phase injection technique also does not allow precise control of the isotropy of the properties of the test zone, in particular because the air flow allowing the evaporation of the solvent is necessarily directional.

In addition, traces of solvent may remain in the adsorbent material, which may interact with the probe molecules or molecules to be analyzed.

In addition, the use of solvents, in particular organic solvents in the case of nitrocellulose, makes the process polluting.

Finally, the bond between the adsorbent material, once solidified, and the base plate is not ensured with certainty. The quality of this bond depends in particular on the chemical compositions of the adsorbent material and of the base plate. The connection between a given analysis zone and the plate may therefore be fragile. In the event of forced circulation of liquid, by means of a relative vacuum, these analysis zones could come off and be carried away by the circulating liquid. It is therefore not possible to carry out an analysis with forced circulation of liquid through the analysis zones obtained by this embodiment. Other processes, using different chemicals or a heating step or an irradiation step, for example, are also described in document WO01/19502A2, after a first lamination step.

In addition to the disadvantages of lamination previously exposed, all these embodiments have the disadvantage of causing physico-chemical modifications of the filtering membrane which alter its essential properties for the analysis and therefore the sensitivity and precision of the analysis.

Insofar as the chemical composition and the physical structure of the membrane on which the analysis is implemented influence the performance of the analysis method, and in particular the quantification limit of this method, the invention therefore aims at proposing a process for the manufacture of a biological analysis chip making it possible to finely control this chemical composition and this physical structure.

In particular, the invention aims at providing a low-cost method for manufacturing an analysis chip, not requiring a heat, chemical or irradiation treatment step for the formation of the test sites in the matrix (except during a possible biochemical functionalization of these sites after or before the formation of the sites) and making it possible to carry out a quantitative analysis of high precision and sensitivity and/or a biological analysis or a simple filtration of a liquid sample.

SUMMARY OF THE INVENTION

The invention relates to a method for manufacturing a biological sample analysis chip comprising:

a—two support matrices are provided, each formed in a solid support material, each having a lower surface and an upper surface and in each of which at least one hole has been formed therethrough between said lower and upper surfaces, among which a lower support matrix and an upper support matrix are defined;

b—at least one sheet of solid and porous analysis material is provided, said sheet having a lower surface and an upper surface, c—the lower support matrix, the sheet of analysis material and the upper support matrix are superimposed in this order so that:

the upper surface of the lower support matrix faces the lower surface of the upper support matrix, the at least one through hole of the lower support matrix is opposite the at least one through hole of the upper support matrix, and the sheet of analysis material is inserted between the lower and upper support matrices;

d—a mechanical assembly of the two support matrices and the sheet of analysis material is carried out during which a pressing force in a direction normal to the lower and upper surfaces of the support matrices is exerted so as to bring the support matrices closer to one another.

Thanks to this arrangement, at least one portion of analysis material closes off at least one channel formed by a through hole of the upper support matrix and a through hole of the lower support matrix which are superimposed. Such a portion is referred to below as an analysis "pad". It is possible to carry out a filtration or an analysis of a biological sample on an analysis pad.

The assembly between the sheet of analysis material and the support matrices is not obtained by a chemical process, nor by melting one of the materials so that the physical and chemical properties of the support and analysis materials before the assembly are not or at least are very little altered after assembly, including near the interface between these two materials. The assembly is obtained only mechanically and by the exercise of a pressing force normal to the upper and lower surfaces of the matrix, so that the deformation of the materials is uniform in a plane normal to the direction of the pressing force. The method therefore makes it possible, unlike the methods implementing a lamination step, not to introduce anisotropy into the support material and or the analysis material in a direction normal to the direction of the pressing force, or at least to minimize the induced anisotropies. Such an anisotropy would lead, for example in the case of immunological tests using fluorescent reagents, to inhomogeneous fluorescence on the surface of an analysis pad, which would make the quantitative analysis of the fluorescence signal imprecise.

Thanks to all of these arrangements, the sensitivity and reproducibility of an analysis chip of a biological sample obtained by the method according to the invention are therefore improved compared to chips obtained according to the methods of the prior art.

The fact that the sheet of analysis material is intercalated between two support matrices also makes it possible to obtain a robust chip for the analysis of a biological sample, resistant to a flow of liquid whose circulation is possibly forced.

In addition, the means needed are only mechanical, therefore not very polluting in that they do not include solvent and they are simple to implement.

According to various aspects, it is possible to provide one and/or the other of the characteristics below taken alone or in combination.

According to one embodiment of the method for manufacturing a biological sample analysis chip, in step b at least two sheets of different analysis material are provided and at the end of step c, the at least two sheets of analysis material are juxtaposed or superimposed.

Thanks to this arrangement, it is possible to form at least two analysis pads whose properties are different so as to carry out two different analyzes on a given sample (in the case where the two sheets of analysis material are superimposed) or two different analyzes on two different samples (in the case where the two sheets of analysis material are juxtaposed)

According to one embodiment of the method for manufacturing a biological sample analysis chip, the pressing force is exerted by means of a vice. Thanks to this arrangement, the pressing force exerted for the assembly can be distributed evenly over the surfaces on which it is exerted. This embodiment makes it possible to minimize the appearance of a non-native anisotropy in the materials which constitute the biological sample analysis chip.

According to one embodiment of the method for manufacturing a biological sample analysis chip, the support material is hydrophobic and the analysis material is hydrophilic or vice versa. In this way, it is for example possible to deposit on the pad a sample to be tested in aqueous phase without it diffusing towards the support material if the latter is hydrophobic. Conversely, if the support material is hydrophilic, the analysis material is hydrophobic and it is then possible to deposit an organic phase sample to be tested on the pad without it diffusing towards the support material.

According to one embodiment of the method for manufacturing a biological sample analysis chip, one proceeds to the functionalization of at least a part of the sheet of analysis material at the end of the mechanical assembly of the two support matrices and of the sheet of analysis material. One can for example consider a biochemical functionalization, by means of an antibody or an antigen which is adsorbed on the pad. In this way, the analysis chip obtained by the method makes it possible to implement an analysis test implementing the reagent used for the functionalization, for example an immunological test on a pad contained in the part of the sheet of analysis material which has been functionalized. Analysis chips can therefore be produced in series before the functionalization step and each functionalized at will at the time of the analysis.

According to one embodiment of the method for manufacturing a biological sample analysis chip, one proceeds to the functionalization of at least part of the analysis sheet before its intercalation between the lower and upper support matrices Thanks to this arrangement, the functionalization can be done on the whole of a sheet of analysis material before cutting the pad. This saves time when the analysis chips are prepared in series. The control of the functionalization, and in particular of a quantity of analysis reagent deposited on each pad, is also better, which ultimately allows better precision and better reproducibility of the tests carried out with a given series of analysis chips.

According to one embodiment of the method for manufacturing a biological sample analysis chip, the upper surface of the lower support matrix and the lower surface of the upper support matrix receive a hydrophobic treatment before the intercalation of the sheet of analysis material between the lower and upper support matrices. In this way, it is possible to form hydrophilic analysis pellets inserted into channels bordered by two support matrices whose hydrophobicity is homogeneous and whose hydrophobic treatment cannot diffuse anisotropically towards the analysis material.

According to one embodiment of the method for manufacturing a biological sample analysis chip, the mechanical assembly of the two support matrices and of the sheet of analysis material results in a crimping of at least a portion of the sheet of analysis material by the upper and lower support matrices.

Thanks to this arrangement, the pad at least partially crimps the matrix so that the assembly of the pad to the matrix will have a particularly high mechanical resistance and it will not be affected by the flow of a liquid sample to be analyzed in the direction normal to the upper and lower surfaces of the matrix, or even by a relative vacuum applied on the side of one of these surfaces in order to accelerate the flow of the liquid sample.

The invention also relates to a biological sample analysis chip comprising:

a lower support matrix formed in a solid support material, having a lower surface and an upper surface and in which at least one through hole has been formed extending between said lower and upper surfaces;

a sheet of solid and porous analysis material, the sheet presenting a lower surface and an upper surface, the biological sample analysis chip further comprising an upper support matrix formed in a solid support material, presenting a lower surface and an upper surface and in which at least one through hole has been formed extending between said lower and upper surfaces, the sheet of analysis material being assembled with and intercalated between the lower and upper support matrices and the at least one through hole of the upper support matrix facing the other at least one through hole of the lower support matrix Such a biological sample analysis chip has the advantage of not containing any residue of solvent or zone of fusion or soldering which could alter the precision of a test carried out with this chip. The assembly of the sheet of analysis material sandwiched between the two support matrices makes it possible both to preserve the native physico-chemical properties of the support material and of the analysis material at the level of an analysis pad. It also makes it possible to carry out a test with flow of a sample along the axis of the through hole from one side of the pad to the other, since the assembly between the pad and the matrix has good mechanical resistance.

According to one embodiment of the biological sample analysis chip, the support material in which the lower support matrix and/or the upper support matrix is formed comprises at least one component chosen from a metal, a plastic material and the cellulose and the analysis material from which the sheet of analysis material is formed comprises at least one component chosen from nitrocellulose, cellulose and an organic polymer.

Such materials are inexpensive and have the necessary qualities of biochemical inertness and adsorption to implement analyzes such as biochemical tests.

According to one embodiment of the biological sample analysis chip, the assembly of the analysis sheet and the support matrices resists at least a relative vacuum equal to 0.100 bar. Thanks to this arrangement, it is possible to carry out an analysis on a sample flowing in a forced manner through an analysis pad without the pad separating from the matrix due to the overpressures which are exerted locally.

According to one embodiment of the biological sample analysis chip, at least part of the sheet of analysis material is functionalized.

The invention also relates to a device for analyzing a biological sample comprising at least one biological sample analysis chip, of which at least part of the sheet of analysis material is functionalized and at least one biological sample analysis chip whose sheet of analysis material is configured to provide filtration. It is thus possible to analyze a blood sample without prior centrifugation, the red blood cells being retained by the filtering analysis chip while the serum or plasma passes through this chip to then be analyzed by the functionalized analysis chip.

The invention also relates to a diagnostic kit comprising at least one biological sample analysis chip according to one of the preceding embodiments and at least one analysis reagent.

One or more analysis reagents, in particular a buffer, a solvent, an antigen, an antibody, can thus be provided in order to carry out a test, such as an immunological test, standardized.

The invention also relates to the use of an analysis chip according to one of the preceding embodiments for diagnostic purposes or for an immunological test.

The invention finally relates to a device for manufacturing a biological sample analysis chip according to one of the preceding embodiments, the manufacturing device comprising:

a system for mechanical assembly of the two lower and upper support matrices and the sheet of analysis material intercalated between the two lower and upper support matrices by means of which a pressing force in a direction normal to the lower and upper surfaces of the lower and upper support matrices is exerted so as to bring the support matrices closer to one another.

Such a manufacturing device is simple to implement and introduces only minimal and isotropic deformation of the support and/or analysis material in any plane parallel to the lower and upper surfaces of the matrix. It therefore makes it possible to form analysis chips at low cost and while preserving the native physico-chemical properties of the support and analysis materials.

BRIEF DESCRIPTION OF DRAWINGS

Embodiments of the invention will be described below with reference to the drawings, briefly described below.

Figure 1:
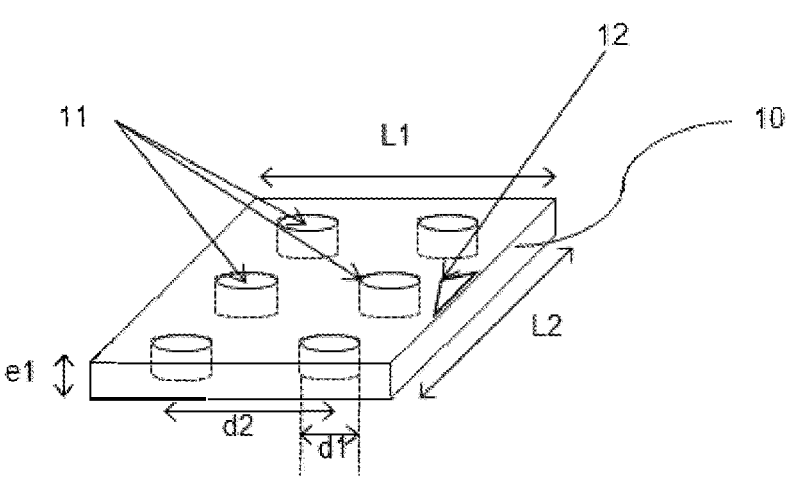
FIG. 1 shows a lower or upper support matrix.

In the drawings, identical references designate identical or similar objects.

DETAILED DESCRIPTION

The invention relates to a method for manufacturing a biological sample analysis chip 1 intended to be implemented in isolation or in an analysis device 7. The analysis device 7—or the biological sample analysis chip 1 on its own—makes it possible, for example, to carry out analyzes of biological liquids such as blood or a liquid fraction of blood (plasma, serum), the urine, saliva, etc.

The analyzed liquid can also be a reaction medium comprising bio-molecules such as antibodies or proteins.

The notion of analysis of a biological sample must therefore be understood in the broad sense, i.e. it is an analysis involving at least one biomolecule among the reagent(s) and/or the analytes.

The biological sample analysis chips 1 can thus be used to detect and quantify complex biomolecules in biological media: blood, plasma, serum, organs or organ extracts, reaction medium in which complex biomolecules are produced (antibodies, proteins).

In particular, the biological analysis can be an immunological test such as an ELISA ("Enzyme-Linked ImmunoSorbent Assay") test.

The biological sample analysis chips 1 can also be implemented in the field of the food industry for the search for pathogenic agents, for example during health checks.

The method for manufacturing a biological sample analysis chip 1 comprises:

a—two support matrices 10 are provided, each formed in a solid support material, which has a lower surface and an upper surface and in each of which a at least one through hole 11 has been formed extending between the lower and upper surfaces, among which a lower support matrix 10a and an upper support matrix 10b are defined;

b—a sheet 13 of solid and porous analysis material is provided, the sheet of analysis material 13 having a lower surface and an upper surface, c—the lower support matrix 10a, the sheet 13 of analysis material and the upper support matrix 10b are superimposed so:

that the upper surface of the lower matrix 10a faces the lower surface of the upper matrix 10b, that at least one through hole 11 of the lower support matrix 10a is facing at least at least one through hole 11 of the upper support matrix 10b, And that the sheet of analysis material 13 is intercalated between the lower and upper matrices;

d—a mechanical assembly of the two support matrices 10 and of the sheet of analysis material 13 is carried out during which a pressing force in a direction normal to the lower and upper surfaces of the matrices 10 is exerted so as to bring the support matrices 10 closer to one another.

The biological sample analysis chip 1 obtained at the end of the process therefore comprises:

a lower support matrix 10a formed in a solid support material and in which at least one through hole 11 has been formed, a sheet 13 of solid and porous analysis material, An upper support matrix 10b formed in a solid support material and in which at least one through hole 11 has been formed.

In the analysis chip, the sheet of analysis material 13 is assembled with and intercalated between the lower 10a and upper 10b support matrices.

Figure 2:
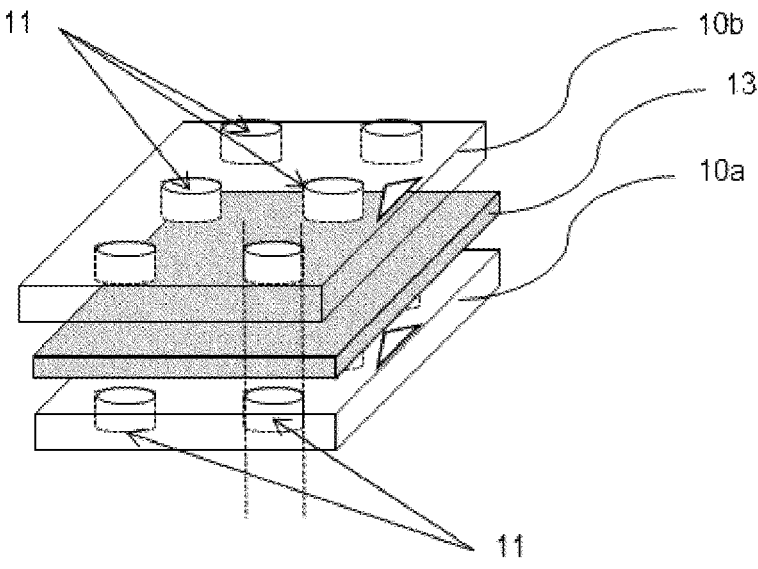
FIG. 2 shows a lower matrix, an upper matrix, and a sheet of analysis material being positioned for assembly to form an analysis chip.

A particular embodiment of a support matrix 10 is shown in FIG. 1. FIG. 2 shows a lower support matrix 10a, a sheet of analysis material 13 and an upper matrix 10b being superimposed, as described in step c.

Figure 3:
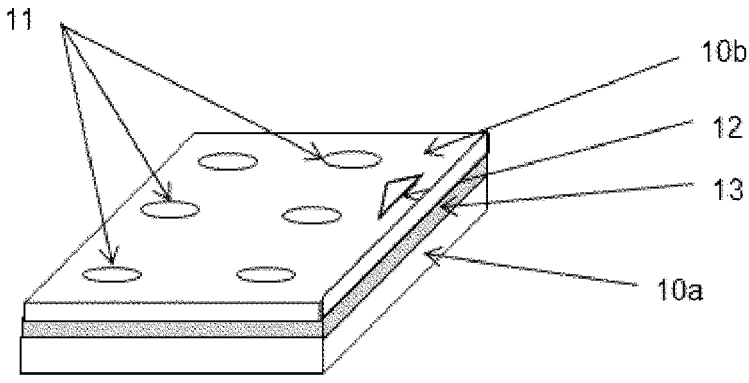
FIG. 3 represents the elements of FIG. 1 after their assembly to form an analysis chip.

The analysis chip 1, which can be observed in a particular embodiment in FIG. 3, therefore comprises a lower support matrix 10a formed in a solid material of thickness e1 in which one or more through holes 11 have been formed, and an upper support matrix 10b formed in a solid material of thickness e'1 in which one or more through holes 11 have been formed.

In a particular embodiment, the materials used to form the lower 10a and upper 10b support matrices are identical. Alternatively, two different materials may be used to form the lower 10a and upper 10b support matrices.

Figure 5:
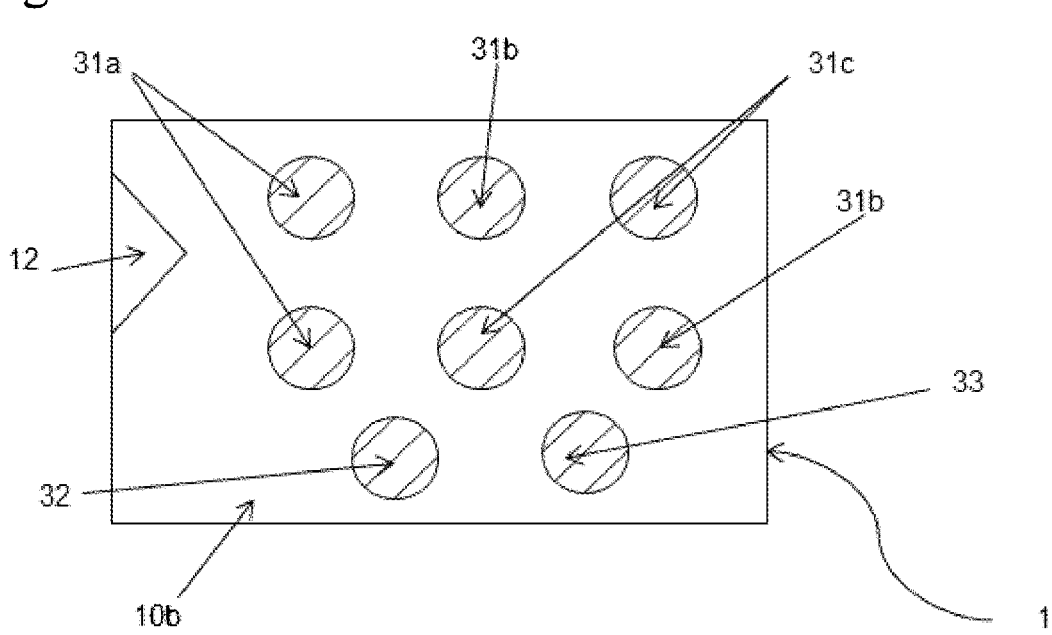
FIG. 5 represents an analysis chip seen from above in a particular embodiment.
Figure 6:
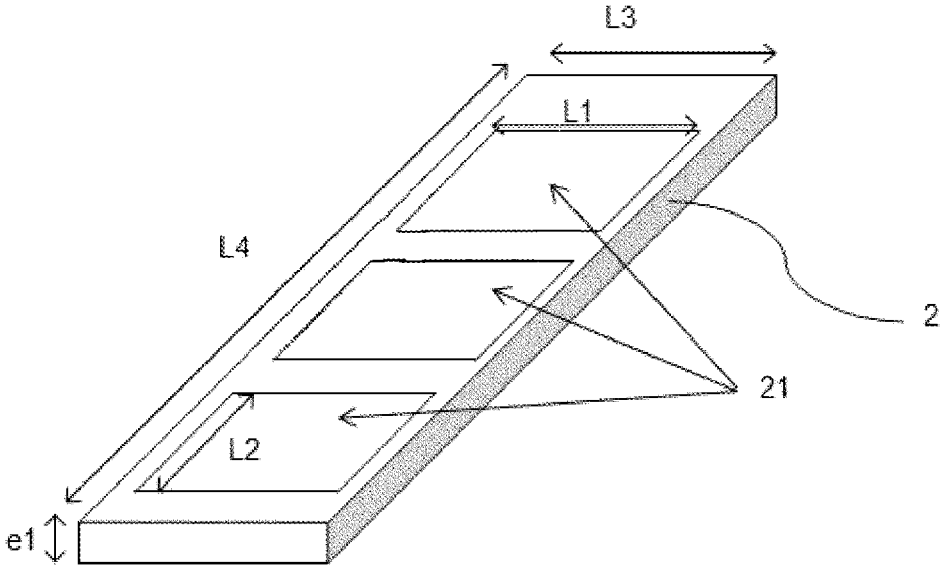
FIG. 6 shows a strip of carrier material with the cut locations of the lower and/or upper matrices.

As shown in FIG. 5, a lower or upper support matrix 10 is formed by cutting out a base part 21, of shape suitable for the analysis device in which it is intended to be used or for its use in isolated manner. The base part 21 is for example a rectangular or square parallelepiped cut from a support strip 2 of a solid material, called in the following "support material", having a lower surface and a flat upper surface parallel to each other.

A base part 21 cut from the support strip 2 to form a support matrix 10 can be a parallelepiped and have a width L1 of between 5 mm (5 millimeters) and 50 mm and a length L2 of between 5 mm and 50 mm. In a particular embodiment, the support matrix 10 is formed in an analysis material of constant thickness e1 between the lower surface and the upper surface, these surfaces being in this case flat and parallel to each other.

The thickness e1 of the support strip 2 is then constant and identical to that of the cut part 21. It is preferably smaller, for example by at least a factor of ten, than the other dimensions (length L1 and width L2) of the cut par 21.

The support strip 2 can for example have a width L3 either identical to or slightly greater than the width L1 of the support matrix 10, or for example greater than twice the width L1.

In the latter case, it is possible to cut out several base parts 21 in the width of the support strip 2.

The width L3 of the support strip 2 is thus for example between 5 mm and 50 mm.

The length L4 of the support strip 2 can be greater, or even much greater, than the length L2 of the part 21.

The length L4 for example greater than 1 m or even 10 m.

In this way, it is possible to successively cut out several base parts 21 in the support strip 2.

The cutting of a base part 21 can for example be carried out by means of a punch in which the support strip 2 is inserted.

If the support strip 2 is long enough, the cutting of the base parts 21 can be automated, the support strip 2 being translated by an adequate distance between two successive cuts of a base part 21.

The thickness e1 of the support strip 2 (and of a base part 21 cut from this support strip 2) can be less than 1 mm, less than 0.15 mm, or even less than 0.1 mm. For example, the thickness e1 of the support strip can be equal to 0.06 mm.

In a particular embodiment, the support strip 2 has a width of 20 mm and a length of 25 m for example. The width and length can be changed according to the type of analysis chips 1 to be manufactured. The thickness of the support strip 2 can be equal to 0.06 mm, i.e. half the current thickness of the filtration membranes (generally made of nitrocellulose) formed in the analysis material, but it could also be of the order 0.10 mm.

In a particular embodiment, a base part 21 is a square filtering membrane with sides of 20 mm.

The support strip 2 can in particular be made of metal, for example steel, copper or brass.

The support strip 2 can, in an alternative embodiment, be made of plastic. By way of non-limiting example, the plastic material can be polyethylene, polyvinyl chloride, polystyrene, polymethyl methacrylate, polypropylene or any other plastic material commonly used in the field of biochemical analyses. It may have undergone a surface treatment and/or be UV resistant. The support material may also contain vegetable fibres, for example cellulose. It may in particular be paper.

The support material is strong but not necessarily rigid. The support strip 2 can thus have a certain flexibility, provided that the support strip 2 or a support matrix 10 formed from this support strip 2 can be manipulated and moved for the preparation of the analysis chips 1, in particular without tearing, also in the case where the preparation of the support matrix 10 is automated. By way of example, photocopier paper Rex Copy A4 distributed by Mondi®, with a weight of 80 g/m², available on the priority date of this patent application, is suitable for the invention.

In the case where the support strip 2 is flexible, the material is sufficiently rigid for the upper and lower surfaces to be effectively flat when the lower surface is, at least locally, simply placed on a flat support. In one embodiment, the support material is rigid enough to allow the cutting of one or more base parts 21 by means of a punch.

In a base part 21 of support material, at least one through hole 11 is formed through the material in its thickness, that is to say along the direction normal to the lower and upper surfaces of the part 21.

In a particular embodiment, a through hole 11 is formed by means of a punch system, comprising one or more individual punches which are identical or of different shapes. In this embodiment, the punch system is translated in the direction of the axis of the future through hole 11, so as to pierce the support matrix 10. A dedicated cutting guide can be placed under the support strip 2.

In a particular embodiment, the through holes 11 are formed on the locations corresponding to the future base parts 21 in the support strip 2 before one or more base parts 21 are cut out.

In another embodiment, the through holes 11 are formed in a base part 21 already cut out.

Alternatively, the through holes 11 are formed at the same time as the part 21 is cut, for example by means of a punch of suitable shape.

The shape of the through holes 11 can be chosen according to the needs of the analysis. For example, the surface delimiting the interior of a through-hole 11 is a cylinder whose generatrix is parallel to the direction normal to the lower and upper surfaces of the part 21, direction which will be referred to below as the "axis of the hole 11" and which will be denoted (Z'Z) in the figures.

For example, the through holes 11 are cylinders of revolution.

Figure 8:
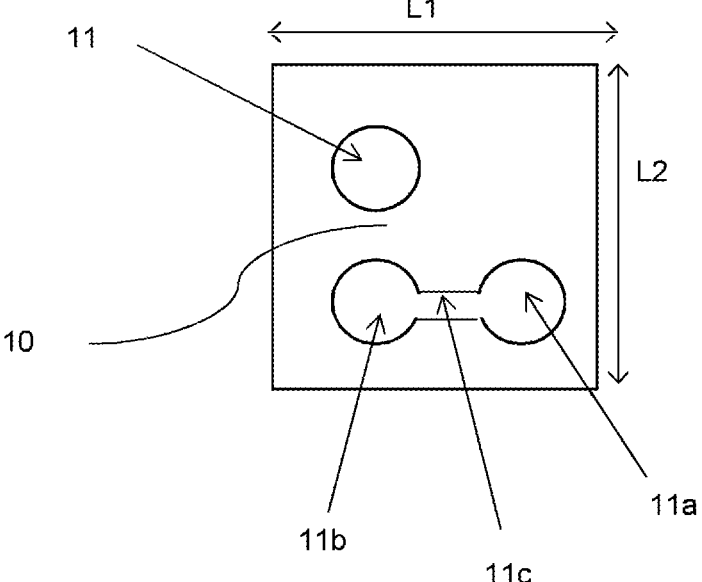
FIG. 8 shows a lower or upper support matrix in a particular embodiment.

In the embodiment represented in FIG. 8, one of the through-holes 11 can be analyzed as formed by two through-sub-parts of circular section 11*a* and 11*b*, connected by a channel 11*c*. Once the pads of analysis material have been inserted as described below, it will thus be possible to deposit the sample to be analyzed in the well corresponding to the first "sub-hole" and to let the sample diffuse from the sub-part 11*a* to sub-part 11*b*. In this case, it is possible to use the analysis chip to perform a test of lateral flow type.

The characteristic dimensions of a through hole 11 in a direction of the upper or lower surface of the part 21 in which the through hole 11 is formed may be less than 1 mm.

For example, a support matrix 10 can comprise 9, 12, 24, 48 or 96 holes (also called "wells") 11 having the shape of cylinders of revolution with a diameter d1 of the order of 300 to 800 μm (micrometers), two successive through holes 11 being spaced apart by a distance d2 of the order of 100 to 250 μm.

In a particular embodiment, 25 through holes 11 of 500 micrometers in diameter are formed spaced 200 micrometers apart, contained in a 6 mm×6 mm square placed in the center of a base part 21 in the shape of a square of support material (20×20 mm).

The punch tool will therefore in this case include 25 punches with a diameter of 500 micrometers. For other configurations of the biological sample analysis chip 1, the punches used for all the through holes 11 or for part of these through holes 11 may have different diameters. The diameter (or a characteristic dimension in the case where the section of the through hole 11 is not circular) of the punch may thus be less than 1000 micrometers, less than 900 micrometers, less than 800 micrometers, less than 700 micrometers, less than 600 micrometers, less than 500 micrometers, less than 400 micrometers, less than 300 micrometers, less than 200 micrometers, less than 150 micrometers, less than 100 micrometers.

Optionally, a cutout or a reference mark 12 is formed on the support matrix 10 so as to be able to identify its orientation, in particular during an analysis which will be carried out later or to facilitate the positioning of a lower support matrix 10*a* opposite an upper support matrix 10*b*.

This arrangement makes it possible to differentiate the through holes 11 from each other when the support matrix 10 has elements of symmetry.

In the first step of the process according to the invention, there is therefore provided:

a lower support matrix 10a formed in a support material of constant thickness e1 between a lower surface and an upper surface and in which one or more through holes 11 have been drilled, and an upper support matrix 10b formed in a support material of constant thickness e'1 between a lower surface and an upper surface in which one or more through holes 11 have been drilled.

In a second step, a sheet 13 of constant thickness, denoted e2, of a second porous solid material called "analysis material" is provided, having an upper surface and a lower surface.

The analysis material is intended to receive on one of its lower and upper surfaces a liquid sample to be analyzed or filtered, which must then be able to flow towards the other of these surfaces, either spontaneously by simple diffusion, or due to forced circulation of the liquid. The analysis material can therefore be a porous material such as paper, in particular filter paper, that is to say paper with a high alpha-cellulose content (in particular more than 90%, 95%, or even 98% of alpha-cellulose).

The analysis material can also be nitrocellulose.

Nitrocellulose has a good affinity for small proteins, peptides or nucleic acids. It is therefore particularly well suited for biological analyses. These examples should not, however, be considered as limiting.

The material for analysis can be chosen in particular according to its resistance to humidity, its filtration rate, its breaking strength, its rate of capillary rise or its resistance to the passage of air.

In the case where the liquid to be analyzed mainly contains water, the analysis material is preferably hydrophilic, so that the liquid to be analyzed wets the surface of the analysis material. In this case, the support material of the lower support matrix 10a and/or of the upper support matrix 10b can be hydrophobic.

In what follows, we will consider that a material is hydrophobic if the water does not wet the material, i.e. if the angle between a drop of water and the surface of the material on which the drop is deposited is strictly greater than 90°. Otherwise, the analytical material is hydrophilic.

The support material can be rendered hydrophobic before the step of assembling a support matrix 10 to a sheet 13 of analysis material by means of a surface treatment, in particular by coating with a wax.

Alternatively, the analysis material can be hydrophobic and the support materials hydrophilic. The analysis material can be an isotropic or anisotropic filter membrane. In particular, it may be an organic filter membrane, that is to say a membrane comprising an organic polymer such as cellulose acetate, a polysulfone or a polyamide. The thickness e2 of the analysis material can be close to the thickness e1 of the support material. The thickness e2 can be greater than, equal to or less than the thickness e1.

In the case where the support material is nitrocellulose, the thickness e2 of the analysis material may thus be of the order of a few hundreds, or even a few tens of micrometers, for example 50 µm to 150 µm. In a third step, the lower support matrix 10a, the sheet 13 of analysis material and the upper support matrix 10b are superimposed in this order so:

that the upper surface of the lower matrix 10a faces the lower surface of the upper matrix 10b, that at least one through hole 11 of the lower support matrix 10a is facing at least one through hole 11 of the upper support matrix 10b, and that the analysis sheet is inserted between the lower 10a and upper 10b support matrices.

At the end of this step, a pressing force in the direction normal to the lower and upper surfaces of the support matrices 10a and 10b is exerted so as to bring these support matrices closer to one another and to obtain the assembly of the support matrices 10a and 10b with the sheet of analysis material 13 and/or between them.

This pressing force can for example be exerted by means of a vice whose lower jaw 9a is placed under the lower support matrix 10a and the upper jaw 9b is placed above the upper support matrix 10b. The vice may be replaced by an equivalent mechanical device.

At the end of the process, the two support matrices 10 and the sheet of analysis material 13 are permanently assembled, that is to say that, under normal conditions of use of the biological sample analysis chip 1, in particular due to the flow of a sample, the chip does not disassemble.

The two support matrices 10 and the sheet of analysis material 13 therefore form a continuum. As a result, at least one through hole 11 of the lower support matrix 10a is therefore in fluid continuity with a through hole 11 of the upper support matrix 10b with which it forms a channel within which a portion of the sheet of analysis material 13 is inserted. In this way if a sample is injected into the through hole 11 of the upper support matrix 10b, it will necessarily pass through the analysis material 13 and then flow through the through hole 11 of the lower support matrix 10a.

A channel is therefore formed from two through holes 11 of the lower support matrix and the upper support matrix superimposed, closed by the analysis material through which the sample to be analyzed can diffuse spontaneously or in a forced manner.

The portion of analysis material closing off a channel formed by a through hole 11 of the upper support matrix 10b and a through hole 11 of the lower support matrix 10a which are superimposed will be referred to below as an analysis "pad" 3. It is on this pad 3 that the analysis of a liquid sample can be carried out.

The way in which the analysis material 13 fits into the through-holes and between the two support matrices depends on the nature of the used support and analysis materials as well as on the intensity of the pressing force exerted. Two particular, non-limiting embodiments are represented in FIGS. 4a and 4b.

Figure 4A:
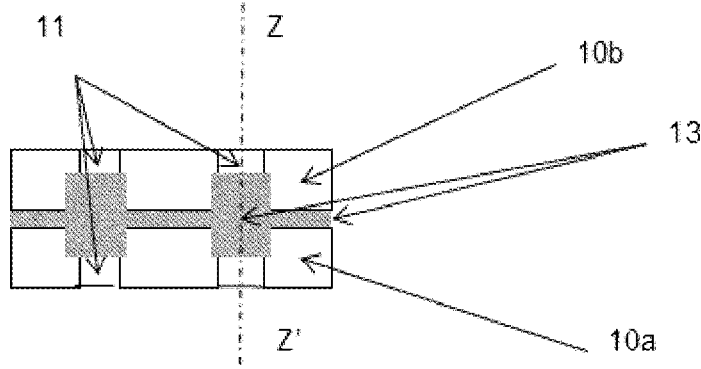
FIG. 4a shows a cross-sectional view of the analysis chip of FIG. 3 in a plane containing the axis of a through-hole in a first embodiment.
Figure 4B:
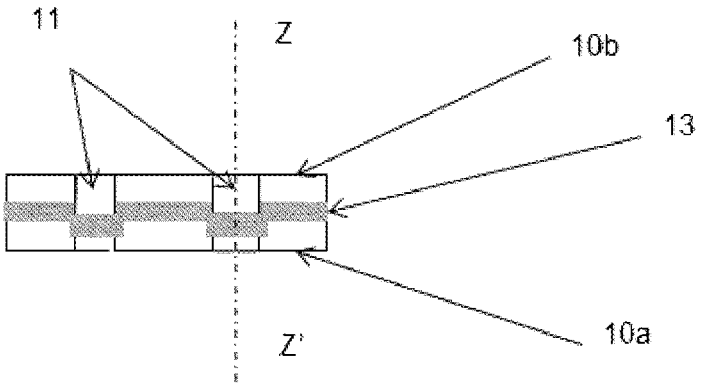
FIG. 4b shows a cross-sectional view of the analysis chip of FIG. 3 in a plane containing the axis of a through-hole in a first embodiment.

In particular, the analysis material may tend to sink into the lower support matrix, as in FIG. 4b, or spread towards both the lower and upper support matrices, as in FIG. 4a.

The analysis material may not be flush with the lower surface of the lower support matrix 10a and/or with the upper surface of the upper support matrix 10b or on the contrary be flush with the level of these two surfaces simultaneously.

Whatever the case, the pressing force exerted for the assembly can be chosen so that the continuity of the sheet of analysis material 13 is not broken due to the insertion of the analysis material in the through holes 11. In this case, the holding in place of the analysis pad 3 is at least ensured by its connection with the rest of the sheet of analysis material 13.

In this case again, it may be desirable to limit the diffusion of the sample to be analyzed from a pad 3 to the rest of the sheet of analysis material. If the sample to be analyzed is in the aqueous phase, the faces of the support matrices 10 intended to be in contact with the analysis sheet may for example be treated with a hydrophobic surface treatment. During assembly, the hydrophobic surface treatment may diffuse under the effect of the pressing force in the sheet of analysis material 13, with the exception of the analysis pad(s) 3, which are located opposite through holes 11. Consequently, the analysis pads 3 will remain hydrophilic while the rest of the analysis sheet 13 will be hydrophobic, which makes it possible to limit the lateral diffusion of the sample to be analyzed outside the analysis pad 3 and thus allows good sensitivity and good reproducibility of the tests carried out on the biological sample analysis chip 1.

The pressing force exerted for the assembly can also be chosen so that the lower 10*a* and upper 10*b* support matrices crimp the portion of the sheet of analysis material 13 closing off a channel formed by a through hole 11 of the upper support matrix 10*b* and a superimposed through hole 11 of the lower support matrix 10*a*. In this case, the holding in place of an analysis pad 3 is at least ensured by this crimping.

If the pressure exerted for assembly is sufficient, the continuity of the sheet of analysis material 13 can be broken by crimping. In this case, it is not possible for the sample to be analyzed to diffuse from an analysis pad 3 to the rest of the biological sample analysis chip 1. This embodiment therefore allows good sensitivity and good reproducibility of the tests carried out on the biological sample analysis chip 1. The height of the pad 3 can in any case be equal to the height of the channel formed by a through hole 11 of the upper support matrix 10*b* and a superimposed through hole 11 of the lower support matrix 10*a*, or even different from this height, as seen in FIGS. 4*a* and 4*b*.

In the case where the pressing force allowing the assembly of the support matrices 10 to the sheet of analysis material 13 is exerted by means of a vice, it is understood that the pressing force may not include a component in a direction normal to the axis of a through hole 11. In other words, the direction of the pressing force is collinear with the axis of a through hole 11, so that no non-native anisotropy is introduced into the support and analysis materials in a direction non-collinear with the axis of the through hole 11. This arrangement makes it possible in particular to precisely control the quantification limit of the analysis chip.

Figure 9:
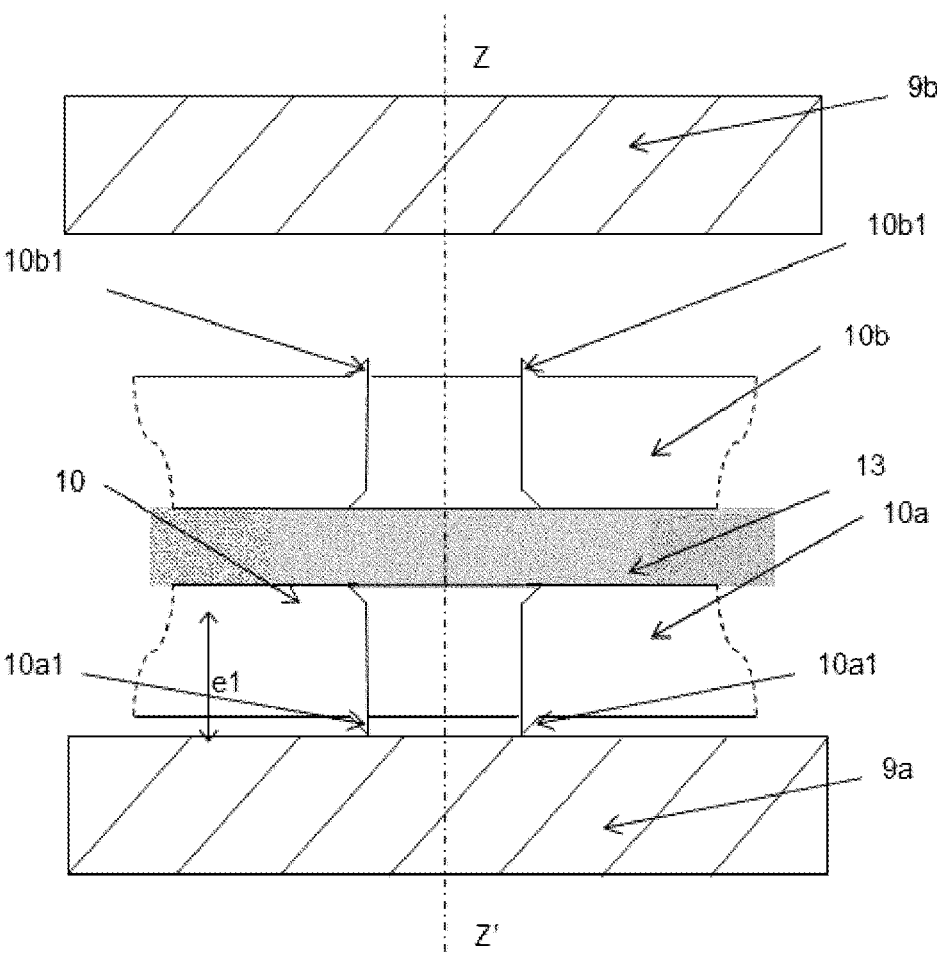
FIG. 9 shows a sheet of analysis material sandwiched between two support matrices in which overhangs have been formed just before assembly using a vice. The overhangs have been deliberately exaggerated to facilitate understanding of the process.

It will be noted that if the through hole 11 has been formed in the material of the lower support matrix 10*a* by means of a punch, an overhang 10*a*1 may have formed at the end of the drilling step which may be folded during the assembly step under the sheet of analysis material so as to ensure its crimping. The same reasoning applies by symmetry for the upper support matrix 10*b*. This case will be understood with the help of FIG. 9 which represents a sheet of analysis material inserted between two support matrices in which overhangs 10*a*1 (respectively 10*b*1) have been formed just before assembly. At the end of the assembly, the overhangs 10*a*1 (respectively 10*b*1) will be folded below (respectively above) the sheet of analysis material.

Whatever the embodiment chosen for the assembly step, no force non-collinear to the axis of a through hole 11 is exerted, so as to maintain unchanged the properties of the material under analysis during this step.

In particular, the method according to the invention has the advantage of not implementing any step which could introduce an anisotropy of the properties of this material and thus degrade the precision and sensitivity of the analysis, as discussed previously for a step of rolling.

The mechanical assembly step can therefore result in a crimping of at least a portion of the sheet of analysis material 13 (forming an analysis pad 3) by the lower 10*a* and upper 10*b* support matrices. During the assembly step, exerting a single mechanical action, the latter being moreover exerted in the direction of the axis of a through hole 11 and possibly distributed uniformly on the lower 10*a* and upper support matrices, makes it possible to maintain the uniformity and the isotropy of the physico-chemical properties of the analysis material in the planes normal to the axis of the hole. The pressure exerted during this assembly step as well as the duration during which this pressure is exerted can be chosen according to the mechanical resistance of the assembly necessary for the analyses.

For example, it is possible to obtain a biological sample analysis chip 1 whose analysis pads 3 remain in place when a fluid passes through them in a forced manner by means of a pressure difference between the upstream face and the downstream face of the pad of less than 100 mbar (millibar); less than 200 mbar; less than 300 mbar; less than 400 mbar; less than 500 mbar; less than 600 mbar; less than 650 mbar; less than 700 mbar; less than 750 mbar; less than 800 mbar; less than 850 mbar; less than 900 mbar; less than 950 mbar; less than 1.00 bar.

The upstream and downstream faces are understood here relative to the direction of fluid flow.

It is considered that an analysis pad 3 "remains in place" if, at the end of the analysis, this analysis pad still completely closes the through hole 11 in which it was inserted. In particular, a shift of the pad 3 in the direction of the axis of the through hole due to the pressure difference between its upstream and downstream faces can occur without questioning the quality of the analysis carried out by means of the biological sample analysis chip 1.

If the analysis pad 3 "stays in place" when a pressure difference exists between its upstream and downstream faces, it will then be said that the biological sample analysis chip 1 "resists" the corresponding relative vacuum.

The upper face of an analysis pad 3 can, in a particular embodiment, simply be subjected to atmospheric pressure and the lower face placed under depression. In this way, an analysis device comprising a biological sample analysis chip 1 can be implemented with forced circulation of fluid, which makes it possible to control the contact time of the sample to be tested with a pad 3 and therefore the reproducibility of the analysis.

This arrangement also makes it possible to reduce the duration of the analyses.

In particular, the forced circulation of the sample to be tested avoids, or at least accelerates, the washing steps generally necessary to eliminate the fraction of the test sample which has not reacted as well as the molecules which have adsorbed in a non-specific way on the membrane.

For example, it is possible to perform a blood test over a period of 30 minutes between the deposit of the sample (not centrifuged) and the result of the analysis.

A conventional ELISA test requires a much longer time, usually 12 to 24 hours.

The mechanical assembly is carried out in the solid phase, and at a temperature below the melting temperatures of the support and analysis materials. This assembly therefore does not implement a process of the welding type, for example, which could distort the materials or modify their physical structure. It also does not implement a solution whose solvent would have to evaporate and whose remaining traces could interfere with the analysis.

Thanks to the assembly method according to the invention, there is no possibility of migration of the support material or of a solvent towards the analysis material and vice versa, so that the analysis material retains its native properties after the properties, i.e. its properties before assembly with the support material.

At the end of the assembly step, it is possible to carry out a functionalization step of one or more pads 3. By way of example, a chosen volume of a solution of probe molecules can be deposited with a pipette or a micropipette, optionally in an automated manner, on one or more pads 3.

The bio-functionalization of a biological sample analysis chip 1 consists in particular in attaching a capture molecule (for example an antibody to detect an antigen) targeting the complex biomolecule to be detected and quantified in the biological liquid to be analyzed.

In a particular embodiment, a roll of biological sample analysis chips 1, in which the pads 3 are already in place, can be placed on a spotting machine. The roll is unrolled to scroll the strips of analysis chips 1 on a filter plate connected to a vacuum pump. The injection head of the "spotting" machine can deposit, for example in 2 or 3 injections, a volume of the order of 10 µL of a solution containing the capture molecule, for example at a concentration of 10 to 30 µg/mL.

The suction vacuum can be chosen to allow a slow filtration over a time of approximately 20 seconds of the 10 µL of solution. All of the pads 3 of each biological sample analysis chip 1 can thus be processed in the same way. A second application can then be carried out under the same conditions but with a solution of BSA (Bovine Serum Albumin) at a concentration of 100 µg/mL. This solution makes it possible to saturate the polar sites of the filtering biological sample analysis chip 1 to avoid non-specific bonds between the biomolecule which will be detected and the analysis surface, for example of nitrocellulose, of the biological sample analysis chip 1.

As a variant, it is possible to carry out the functionalization of a biological sample analysis chip 1 upstream of the assembly. It is thus possible to insert several different sheets of analysis material 13, either superimposed, or offset from each other, or both at the same time, between the lower 10a and upper 10b support matrices.

For example, it is possible to prepare at least two sheets of analysis material 13 which are identical at the start but each having undergone a different bio-functionalization step, in particular by adsorption of two different antigens. A pad 31a on which a first antigen has been adsorbed can be formed in a first channel closed off by a portion of the first sheet of analysis material 13, and another pad 31b on which a second antigen has been adsorbed can be formed in a second channel closed off by a portion of the second sheet of analysis material 13. In this case, a cutout or reference mark 12 optionally formed on the support matrix 10 may help identify the positions of the various test sites.

It is also possible to superimpose two different sheets of analysis material 13, which then both end up one on top of the other, intercalated between the lower 10a and upper 10b support matrices. In this way, a sample to be tested will successively undergo the two tests corresponding to the two sheets of analysis material 13. This embodiment can for example be interesting when it is desired to extract two different analytes from the sample to be analyzed in order to carry out a third test.

If the management of the bio-functionalization is done on the scale of the sheet of analysis material 13, rather than on the scale of the analysis pad 3 on a given biological sample analysis chip 1 and/or on successive analysis chips 1, it is possible to produce in series with a high yield identical analysis chips 1 having identical analytical qualities, making it possible to work under conditions of satisfactory repeatability, even reproducibility.

The limit of quantification, i.e. the smallest concentration or content of the analyte that can be quantified, with an acceptable uncertainty, under the experimental conditions described in the method, can be considered constant for a series of analysis chips produced automatically from the same sheets of analysis material.

This quantification limit is easier to control in the case of a sheet than in the case of a single pad 3 in which the edge effects will play an important role.

It is also possible to orient the probe molecules used for the functionalization so that the sites on which the molecules to be tested can bind are oriented along the axis of the hole. This arrangement makes it possible to further increase the sensitivity (or the limit of quantification) of the analysis. The probe molecules may in particular be those described in patent EP3591024B1 (inventors Wong Ka-Leung, Goetz Joan et al.) filed on Jul. 5, 2018, namely ultra-bright luminescent lanthanide nanoparticles comprising terbium. Quantification limits of the order of a few atoms per microliter of liquid to be tested are thus achieved.

In a particular embodiment, the analysis material is not functionalized and is kept in its native structure at the level of the pads 3. In this way, a so-called "filtering" pad 32 is formed, the sole function of which is a filtration function.

If one superimposes a biological sample analysis chip 1 comprising filtering pads 32 and a biological sample analysis chip 1 comprising functionalized pads 31 (31a, 31b, etc.) so as to that each filtering pad 32 is placed above a functionalized pad 31 so that all the fluid which passes through a filtering pad 32 reaches the corresponding functionalized pad 31, it is thus possible to analyze a blood sample without prior centrifugation, red blood cells being retained by the filtering biological sample analysis chip 1 while the serum or plasma passes through this chip to then be analyzed by the functionalized biological sample analysis chip 1.

This arrangement therefore saves considerable time and material for such analyses. In a particular embodiment, one or more pads 3 can be calibration pads 33 of the biological sample analysis chip 1. After incubation of the roll of analysis chips 1, for example at 37 degrees Celsius for 30 minutes, the analysis chips 1 are ready. They can at this stage be separated from each other with a cutting tool which makes it possible to obtain isolated analysis chips of the same dimensions.

At the end of the assembly step, and possibly after functionalization, it is thus possible, if this has not already been done previously, to cut the base parts 21 to detach the analysis chip(s) 1 of the support strip 2.

A biological sample analysis chip 1 obtained by the method according to the invention can be stored for several months at room temperature, preferably in a dry atmosphere (for example under airtight and watertight protection).

In particular, analysis chips 1 can be stored at 20° C.+/−5° C. for at least 1 month, at least 2 months, at least 3 months, at least 4 months, at least 5 months, at least 6 months, at least 7 months, at least 8 months, at least 9 months, at least 10 months, at least 11 months, at least 12 months without altering their analytical properties.

In particular, a reference test on a reference biological sample will statistically give the same concentration of the analyte sought (same mean and same standard deviation) on a batch of biological sample analysis chips 1 just after manufacture and after storage at 20° C.+/−5° C. under airtight and watertight protection (e.g. blister pack) for at least 1 month, at least 2 months, at least 3 months, at least 4 months, at least 5 months, at least 6 months, at least 7 months, at least 8 months, at least 9 months, at least 10 months, at least 11 months, at least 12 months.

The method for manufacturing a biological sample analysis chip 1 according to the invention makes it possible to control the properties of the support material independently of the properties of the analysis material and vice versa, unlike the methods of the prior art.

Typically, if the support material is formed from a metal plate, this metal plate can be rendered hydrophobic prior to the step of assembling a support matrix 10 to a sheet of analysis material 13. For example, a surface treatment, such as a coating with a natural or synthetic wax, can be implemented.

In the known processes, such a treatment limits the analytical qualities of the chip, since the wax can migrate in an uncontrolled manner from the support material to the analysis material, for example during a heating or chemical treatment or lamination step. The wax (or any other chemical compound used for the surface treatment) can then interfere with the analysis. Among other things, fluorescence quenching phenomena are observed, which reduce the sensitivity of the analysis when fluorescent probe molecules are used. In the invention, the assembly step does not lead to such uncontrolled diffusion or migration of the wax. Certain embodiments even make it possible to avoid an uncontrolled diffusion or migration of chemical species from the analysis pads 3 or towards these pads 3. The method according to the invention therefore makes it possible to obtain a biological sample analysis chip 1 whose test zones (in other words the analysis pads 3) are formed with better precision than with the methods of the prior art. This analysis is also valid for the case where the sheets of analysis material 13 are functionalized before the mechanical assembly step.

We can therefore see the advantage of the method according to the invention, which makes it possible to limit the interference between the support and analysis materials which constitute it, and thus to obtain a biological sample analysis chip 1 with a low limit of quantification.

The process steps can be carried out using simple tools and the mechanical assembly step does not require solvents. The process is therefore inexpensive, rapid, and not very polluting. Insofar as one of the materials among the support and analysis materials can be hydrophilic, it will be possible in a particular embodiment to work under controlled hygrometry conditions for one or more stages of the process, so as to keep a precise control over the geometry and the volume of the support matrix 10 and/or the pads 3 of a biological sample analysis chip 1.

A biological sample analysis chip 1 obtained by the method according to the invention can be implemented in isolation. In this case, a sample to be analyzed can be deposited on one or more of the pads 3 of the chip. Or even several samples to be analyzed can each be deposited on one or more pads 3 different from those used for the other samples, simultaneously or successively.

The chip can, to do this, be placed horizontally, so that a given liquid sample to be analyzed flows from the upper face of the analysis pad 3 on which it has been deposited towards the lower face of this same analysis pad 3, either under the effect of gravity, or under the effect of a pressure gradient, a relative vacuum being applied on the side of the lower face of the analysis pad 3.

Figure 7:
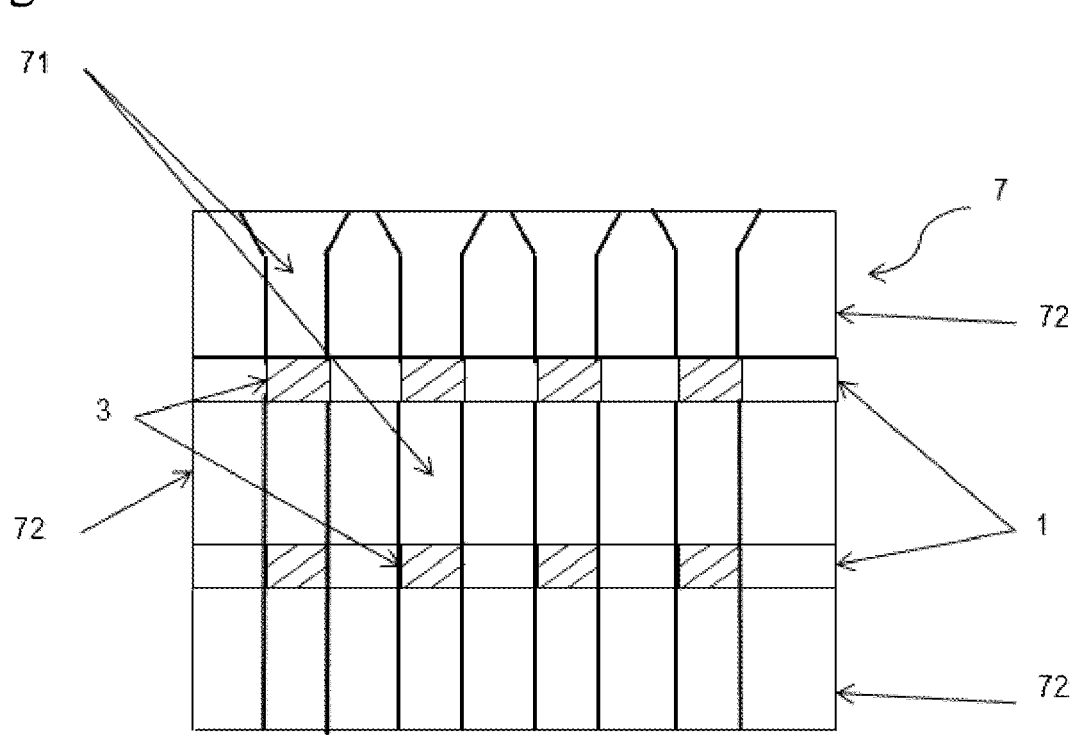
FIG. 7 shows a multiplexed analysis device comprising two analysis chips.

Several analysis chips 1, in particular functionalized differently from each other, can be superimposed in as described in application WO2014/053,237A1, so that different channels are formed, each channel containing a single analysis pad 3 or more analysis pads 3, each of the latter belonging to a different biological sample analysis chip 1. Such a three-dimensional multiplexed analysis device is schematically represented in FIG. 7. The analysis device 7 consists of a stack of solid support plates 72, for example made of polymethyl methacrylate (PMMA) or another plastic material, in which microchannels 71 are formed and between which analysis chips 1 are inserted.

The microchannels are aligned with each other and the analysis sites (that is to say the pads 3) of the analysis chips 1 are inserted between two microchannels of two consecutive support plates 72. It is also possible to superimpose several analysis chips 1 between two consecutive support plates 72. In this case, if different samples to be analyzed are tested in the different channels, it is possible to perform a 3D multiplexed analysis.

More simply, it is possible to provide an analysis device 7 comprising four pillars on which the biological sample analysis chip 1 is fixed by its four corners. These two examples are non-limiting.

The detection of an analyte of interest can be done by an immunological analysis of the ELISA type: once the capture molecule/biomolecule of interest complex has formed on the analysis sites (or equivalent wells) of the biological sample analysis chip 1, a revealing antibody is added which specifically binds to the capture molecule/biomolecule complex. The fluorescence or color that appears in each well is measured using a device such as a photomultiplier or a CMOS-type camera, coupled with a computer program that performs the calculations.

The invention therefore also relates to an analysis device 7 comprising at least one biological sample analysis chip 1. The analysis device 7 can contain several analysis chips 1, in particular superimposed, as described above.

The invention further relates to a diagnostic kit comprising at least one biological sample analysis chip 1.

The diagnostic kit can also comprise a support for the biological sample analysis chip 1 and/or at least one analysis reagent. The analysis reagent may in particular contain one or more antibodies or one or more antigens with a view to implementing an immunological test. The analysis reagent can also be a revealer.

In the case of the present application, the term immunological test ("immunoassay") is understood to mean a test implementing at least one antigen to detect antibodies directed against a pathogenic agent in a sample or at least one antibody to detect an antigen of a pathogen in a sample.

The analysis reagent can also be a buffer, for example a saline phosphate buffer (PBS) or another solution, for example a solution of bovine serum albumin (BSA).

The invention relates to the use of a biological sample analysis chip 1 for diagnostic purposes or for carrying out an immunological test. In particular, serological tests for research and quantification of immunoglobulin G or M type antibodies (IgG or IgM) can be implemented after functionalization of the biological sample analysis chip 1 using the appropriate antigen. The biological sample analysis chip 1 can also be functionalized to search for and quantify heat shock proteins such as the proteins of the HSP60 family by means of a specific antibody, for example a fluorescent one. The apolipoprotein ApoAl or even mediators of inflammation such as C-reactive protein (CRP) or the pancreatic stabilizing protein PSP ("pancreatic stone protein") can be searched by the implementation of an enzymoimmunological method on the biological sample analysis chip 1.

The invention finally relates to a device for manufacturing a biological sample analysis chip 1 according to any one of the embodiments comprising a system for mechanical assembly of the two support matrices and 10*b* and of the sheet of analysis material 13 intercalated between the two support matrices 10*a* and 10*b* by means of which a pressing force in the direction normal to the lower and upper surfaces of the support matrices 10*a* and 10*b* is exerted so as to bring the support matrices 10 closer to one another.

The manufacturing system may in particular comprise a vice. It may also comprise one or more punch systems each comprising one or more individual punches, identical or not and whose stroke is adjustable, and one or more counter-pieces for drilling through holes in the support material.

The device for manufacturing a biological sample analysis chip 1 can be fully automated.

For example, the support strip 2 can be made of metal, eg steel, copper, brass or else of plastic material, provided that the support is rigid enough to allow the various operations which will follow.

Prior to manufacture, the support strip 2 can be treated, for example by spraying its faces with a waxy polymer having the characteristic of a light glue. Then a punch tool and the corresponding counter piece are provided in order to be able to properly perforate the support strip 2 and thus make the wells (or through holes 11) in the support strip 2. This tool can be made of steel so that its rigidity and durability are guaranteed. The dimensions will be adapted to the types of membranes to be produced. In a particular case, 25 through holes 11 of 500 micrometers in diameter are formed spaced 200 micrometers apart, i.e. a square of 6 mm× 6 mm placed in the center of a square biological sample analysis chip 1 of side 20 mm. This punch tool will have 25 pegs (also called "punches") with a diameter of 500 microns. For other membranes, the punches may have different diameters and shapes.

This "punches and counter piece" set is fixed under a press. The support strip 2 unrolls automatically and in adjusted manner in the middle of this "punch and counter-piece" set in order to automatically create wells by simple movement from top to bottom in the intended place. The displacement of the support strip 2 can be calculated so as to have at the output of this stamping all the membranes (or biological sample analysis chips 1) of the same size and that each membrane is clearly delimited from the following one. It is possible to carry out several steps in parallel.

A second support strip 2 will be worked in the same way to obtain one or more upper support matrices 10*b*.

It is then possible to use a double feed by superimposed strips to bring the two strips of prepared support material into a dedicated press. The strips, optionally treated with the hydrophobic polymer treatment, are introduced in such a way that the polymer will be between the two strips of support material, metal or plastic for example A strip of a filter membrane (or even sheet of analysis material 13) of the same size, for example nitrocellulose, is positioned to pass between the two strips of support material, for example metal or plastic, before introduction into a press. The press is lowered automatically with pressure when the three-band system is passing, so that once the pressure is finished there will be at the output a membrane (or biological sample analysis chip 1) which will be composed of three welded parts. The nitrocellulose is thus pressed between the two strips of support material 2, for example made of metal or plastic, filling the free through-holes 11 and being loaded with glue (or hydrophobic polymer) at the non-perforated places. It is, on the one hand, incorporated into the polymer and, on the other hand, it is pushed into the wells of the two strips of support material 2, for example made of metal or plastic. The alignment of the lower 10*a* and upper 10*b* support matrices is such that the wells of the two strips of support material 2, for example metal or plastic, are aligned on entry into the press. After pressing, the strip system is pushed to take out the strips (comprising one or more analysis chips 1) thus formed and a new pressing is carried out to form the following strips.

On leaving the machine, a roll of a strip of support material (steel, copper, brass or plastic) is obtained on which biological sample analysis chips 1 are distributed, comprising for example analysis sites of 300 to 600 micrometers in diameter evenly arranged and spaced from the boundaries of the finished membranes.

The roller can then undergo an automated bio-functionalization step as described above.

LIST OF REFERENCE SIGNS

1: analysis chip
10: lower or upper support matrix
10*a*: lower support matrix
10*a*1: overhang of the lower support matrix
10*b*: upper support matrix
10*a*1: overhang of the upper support matrix
11: hole through a support matrix 10
11*a*, 11*b*: sub-part of a through hole 11
11*c*: channel connecting two sub-parts 11*a* and 11*b*
12: cutout/reference mark
13: sheet of analysis material
2: support strip
21: base part
3: analysis pad
31*a, b, c*: functionalized analysis pad 3
32: filtering pad
33: calibration pad
7: multiplexed analysis device
71: microchannel
72: support plate
9*a*: lower jaw of a vice
9*b*: upper jaw of a vice

The invention claimed is:

1. A method of manufacturing a biological sample analysis chip comprising:

an upper support matrix made of a solid support material, the upper support matrix having, an upper support matrix upper surface, an upper support matrix lower surface and at least one upper support matrix through hole;

a lower support matrix made of the solid support material, the lower support matrix having a lower support matrix upper surface, a lower support matrix upper surface and at least one lower support matrix through hole wherein the lower support matrix upper surface faces the upper support matrix lower surface, each lower support through hole of the at least one lower support matrix through hole aligns with a corresponding upper support through hole of the at least one upper support matrix through hole;

a first sheet made of a first porous solid analysis material, the first sheet having a first sheet upper surface and a first sheet lower surface;

a second sheet made of a second porous solid analysis material different from the first porous solid analysis material, the second sheet having a second sheet upper surface and a second sheet lower surface wherein the first sheet and the second sheet are disposed between the upper support matrix and the lower support matrix;

the method comprising:

assembling a mechanical assembly including the lower support matrix, the upper support matrix, the first sheet and the second sheet wherein the lower support matrix upper surface faces the upper support matrix lower surface and each through hole of the at least one lower support matrix through hole aligns with the corresponding through hole of the at least one upper support matrix through hole;

intercalating the first sheet and the second sheet between the upper support matrix and the lower support matrix; and approximating the upper support matrix and lower support matrix by exerting a pressing force in a direction normal to the support matrix lower surface and the support matrix upper surface thereby providing the biological sample analysis chip.

2. The method according to claim 1 wherein the exerting the pressing force is by means of a vice.

3. The method according to claim 1, wherein the solid support material exhibits hydrophobicity and the first sheet or the second sheet or both exhibits hydrophilicity.

4. The method according to claim 1, further comprising functionalizing at least part of the first sheet or at least part of the second sheet or both after the approximating.

5. The method according to claim 1, further comprising functionalizing the first sheet or at least part of the second sheet or both before the intercalating.

6. The method according to claim 1, further comprising treating the lower support matrix upper surface and the upper support matrix lower surface such that the lower support matrix upper surface and the upper support matrix lower surface exhibits hydrophobicity before the intercalating.

7. The method according to claim 1, further comprising crimping of at least a portion of the first sheet and at least a portion of the second sheet by the lower support matrix and the upper support matrix.

8. A biological sample analysis chip biological sample analysis chip for diagnosing a condition and for performing an immunological test comprising:

an upper support matrix made of a solid support material, the upper support matrix having, an upper support matrix upper surface, an upper support matrix lower surface and at least one upper support matrix through hole;

a lower support matrix made of the solid support material, the lower support matrix having a lower support matrix upper surface, a lower support matrix upper surface and at least one lower support matrix through hole wherein the lower support matrix upper surface faces the upper support matrix lower surface, each lower support through hole of the at least one lower support matrix through hole aligns with a corresponding upper support through hole of the at least one upper support matrix through hole;

a first sheet made of a first porous solid analysis material, the first sheet having a first sheet upper surface and a first sheet lower surface;

a second sheet made of a second porous solid analysis material different from the first porous solid analysis material, the second sheet having a second sheet upper surface and a second sheet lower surface wherein the first sheet and the second sheet are disposed between the upper support matrix and the lower support matrix.

9. The biological sample analysis chip according to claim 8 wherein the solid support material comprises at least one component selected from a metal material, a plastic material and a cellulose material and the first porous solid analysis material and the second porous analysis material each comprise at least one component selected from a nitrocellulose material, a cellulose material and an organic polymer material.

10. The biological sample analysis chip according to claim 8 further configured to resist an internal vacuum pressure of 0.1 bar.

11. The biological sample analysis chip according to claim 8, wherein the first sheet includes a functionalized portion or the second sheet includes a functionalized portion.

12. A biological sample analysis device comprising: the biological sample analysis chip according to claim 11; and a second biological sample analysis chip comprising:

i) a second lower support matrix made of the solid support material and having a second lower support matrix lower surface and a second lower support upper surface and at least one second lower support matrix through hole extending between said second lower support matrix lower surface and said second lower support matrix upper surface;

ii) a third sheet made of a third solid porous material, said third sheet having a third sheet lower surface and a third sheet upper surface;

iii) a second upper support matrix made of the solid support material and having a second upper support matrix lower surface and a second upper support upper surface and at least one second upper support matrix through hole extending between said second upper support matrix lower surface and said upper support matrix upper surface;

wherein the third sheet is between the lower support matrix and the upper support matrix, each second upper support matrix through hole of the at least one second upper support matrix through hole is aligned with a corresponding second lower support matrix through hole of the at least one second lower support matrix through hole and wherein the third sheet is configured to filter a biological sample.

13. A diagnostic kit comprising:

the biological sample analysis chip according to claim 8; and an analysis reagent.

\* \* \* \* \*